(12) United States Patent
Sughrue et al.

(10) Patent No.: US 11,080,484 B1
(45) Date of Patent: Aug. 3, 2021

(54) NATURAL LANGUAGE PROCESSING OF ELECTRONIC RECORDS

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/066,335

(22) Filed: Oct. 8, 2020

(51) Int. Cl.
*G06F 40/284* (2020.01)
*G16H 10/60* (2018.01)

(52) U.S. Cl.
CPC ........... *G06F 40/284* (2020.01); *G16H 10/60* (2018.01)

(58) Field of Classification Search
CPC .............................. G06F 40/284; G16H 10/60
USPC ............................................................. 704/9
See application file for complete search history.

(56) References Cited

U.S. PATENT DOCUMENTS

| | | | | |
|---|---|---|---|---|
| 6,006,188 | A * | 12/1999 | Bogdashevsky | G10L 17/26 704/270 |
| 8,463,595 | B1 * | 6/2013 | Rehling | G06Q 30/02 704/9 |
| 8,606,575 | B1 * | 12/2013 | Witt-ehsani | G10L 15/1822 704/235 |
| 10,593,429 | B2 | 3/2020 | Allen | |
| 10,614,196 | B2 * | 4/2020 | Maitra | G16H 50/70 |
| 2005/0176680 | A1 * | 8/2005 | Lalji | A61K 31/724 514/58 |
| 2007/0142395 | A1 * | 6/2007 | Leventer | A61K 31/496 514/253.07 |
| 2008/0086433 | A1 * | 4/2008 | Schmidtler | G06N 20/10 706/12 |

(Continued)

FOREIGN PATENT DOCUMENTS

WO    WO 2020/006495    1/2020

OTHER PUBLICATIONS

Chandran et al., "Use of Natural Language Processing to identify Obsessive Compulsive Symptoms in patients with schizophrenia, schizoaffective disorder or bipolar disorder," Sci. Rep., 2019, 9:14146.

*Primary Examiner* — Thuykhanh Le
(74) *Attorney, Agent, or Firm* — Fish & Richardson P.C.

(57) ABSTRACT

Electronic records are accessed from computer storage for a given subject, wherein the electronic records include natural language notes about the subject. Tokens are identified in the natural language notes. For each token, a corresponding intensity score is generated representing an intensity of match between the token and a particular dimension, wherein the intensity scores are each values on a first scale, wherein each dimension is one of a plurality of dimensions of a category out of a plurality of categories; generating rescaled-intensity scores from the intensity scores by rescaling the intensity scores from the first scale to a second scale different from the first scale. For each dimension of each category, a dimension-score is compiled based on the intensity scores; and categorizing the subject into at least one category based on the dimension scores. The subject is categorized into at least one category based on the dimension scores.

21 Claims, 4 Drawing Sheets

(56) References Cited

U.S. PATENT DOCUMENTS

| | | | |
|---|---|---|---|
| 2009/0076927 A1* | 3/2009 | Sridhar | G06Q 30/0603 |
| | | | 705/26.1 |
| 2012/0089705 A1* | 4/2012 | French | H04N 7/18 |
| | | | 709/219 |
| 2013/0054244 A1* | 2/2013 | Bao | G10L 13/02 |
| | | | 704/260 |
| 2013/0325437 A1* | 12/2013 | Lehman | G06F 40/30 |
| | | | 704/9 |
| 2014/0046696 A1 | 2/2014 | Higgins et al. | |
| 2014/0181128 A1 | 6/2014 | Riskin et al. | |
| 2014/0221388 A1* | 8/2014 | Kikuchi | A61K 31/135 |
| | | | 514/253.07 |
| 2015/0309987 A1* | 10/2015 | Epstein | G06F 40/279 |
| | | | 704/9 |
| 2016/0124953 A1* | 5/2016 | Cremer | G06F 16/1787 |
| | | | 715/203 |
| 2016/0125873 A1* | 5/2016 | Braho | G10L 15/22 |
| | | | 704/239 |
| 2016/0147796 A1* | 5/2016 | Ardila | G06F 16/211 |
| | | | 707/756 |
| 2016/0148612 A1* | 5/2016 | Guo | G06F 40/237 |
| | | | 704/257 |
| 2016/0162805 A1* | 6/2016 | Kwon | G06N 3/0445 |
| | | | 706/12 |
| 2016/0203124 A1* | 7/2016 | Cuthbert | G06F 40/51 |
| | | | 704/2 |
| 2016/0260143 A1* | 9/2016 | Ekambaram | G06F 3/013 |
| 2016/0314410 A1* | 10/2016 | Carmichael | H04N 21/4668 |
| 2016/0350486 A1 | 12/2016 | Plunkett et al. | |
| 2016/0350487 A1 | 12/2016 | Plunkett et al. | |
| 2016/0371568 A1* | 12/2016 | Tin | G06K 9/6228 |
| 2017/0196501 A1* | 7/2017 | Watson | G16H 40/63 |
| 2017/0236520 A1* | 8/2017 | Borgstrom | G10L 17/04 |
| | | | 704/239 |
| 2018/0060338 A1* | 3/2018 | DeLuca | G06F 16/9535 |
| 2018/0068222 A1* | 3/2018 | Brennan | G06N 5/022 |
| 2018/0068407 A1* | 3/2018 | Sicard | G16H 20/30 |
| 2018/0150882 A1* | 5/2018 | Hu | G06Q 30/0269 |
| 2018/0165554 A1* | 6/2018 | Zhang | G06K 9/6256 |
| 2019/0087408 A1* | 3/2019 | Komine | G06N 5/04 |
| 2019/0102682 A1* | 4/2019 | Jayaraman | G06N 7/005 |
| 2019/0164555 A1* | 5/2019 | Chen | G10L 15/22 |
| 2019/0220777 A1* | 7/2019 | Johnson | G06Q 50/01 |
| 2019/0324537 A1* | 10/2019 | Kaji | G06K 9/00523 |
| 2019/0340425 A1* | 11/2019 | Xu | G06K 9/00302 |
| 2019/0371450 A1* | 12/2019 | Lou | G16H 50/30 |
| 2019/0385711 A1* | 12/2019 | Shriberg | G10L 25/66 |
| 2020/0007634 A1* | 1/2020 | Xie | G06F 17/16 |
| 2020/0065868 A1* | 2/2020 | Garlapati | G06F 40/242 |
| 2020/0090067 A1* | 3/2020 | Anders | G06K 9/00335 |
| 2020/0093856 A1* | 3/2020 | Saito | A61K 9/007 |
| 2020/0188358 A1* | 6/2020 | Loya | A61H 31/137 |
| 2020/0234305 A1* | 7/2020 | Knutsson | G06N 20/00 |
| 2020/0251100 A1* | 8/2020 | Tan | G06F 16/90332 |
| 2020/0279017 A1* | 9/2020 | Norton | G06F 16/36 |
| 2020/0286614 A1* | 9/2020 | Do | G16H 15/00 |

* cited by examiner

NATURAL LANGUAGE PROCESSING OF ELECTRONIC RECORDS

TECHNICAL FIELD

This specification relates to natural-language analysis by a computer on historical records including electronic medical records.

BACKGROUND

Natural language processing (NLP) is a subfield of linguistics, computer science, and artificial intelligence concerned with the interactions between computers and human language, in particular how to program computers to process and analyze large amounts of natural language data. Challenges in natural language processing frequently involve speech recognition, natural language understanding, and natural-language generation.

A natural language or ordinary language is any language that has evolved naturally in humans through use and repetition. Natural languages can take different forms, such as speech or signing. They are distinguished from constructed and formal languages such as those used to program computers or to study logic.

SUMMARY

This specification describes technologies for classifying subjects into behavioral categories based on natural language notes. These technologies generally involve classifying notes about a subject into one or more pre-existing classifications using natural-language analysis of the notes.

In general, one innovative aspect of the subject matter described in this specification can be embodied in methods that include the actions of accessing, from computer storage, electronic records for a given subject, wherein the electronic records include natural language notes about the subject; identifying tokens in the natural language notes; generating, for each token, a corresponding intensity score representing an intensity of match between the token and a particular dimension, wherein the intensity scores are each values on a first scale, wherein each dimension is one of a plurality of dimensions of a category out of a plurality of categories; generating rescaled-intensity scores from the intensity scores by rescaling the intensity scores from the first scale to a second scale different from the first scale; compiling, for each dimension of each category, a dimension-score based on the intensity scores; and categorizing the subject into at least one category based on the dimension scores.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination.

The electronic records are electronic medical records (EMRs) stored in a patient-management system that manages EMRs for many patients. The electronic records comprise documents written by the subject. The natural language notes comprise natural language notes written by a clinician of the subject. Identifying tokens in the natural language notes comprises: generating a list of all possible-tokens in the natural language notes; and selecting some, but not all of the possible-tokens based on a match with a particular dimension. The particular dimension is one dimension that is part of a category from a list of possible categories used by a clinician of the subject, each category having a plurality of dimensions. The second scale is anxiety, the second scale spans from 0 to 9 and the particular category is "Major Depressive Disorder". The tokens comprise words, strings, and portions of words. The first scale spans from 0 to 1. Generating rescaled-intensity scores from the intensity scores by rescaling the intensity scores from the first scale to a second scale different from the first scale comprises only generating rescaled-intensity scores for intensity scores that are greater than a threshold value.

The subject matter described in this specification can be implemented in particular embodiments so as to realize one or more of the following advantages. The technology of computer-based natural-language processing is advanced. The use of natural-language notes as an input to behavior categorization can allow for new and previously-unrealized uses of existing digital data to provide medical services. This technology can provide categorization in clinically accepted categories such as those published in widely used diagnostic manuals. Therefore, this technology can advantageously aid existing clinician by providing information in formats and structures that are already familiar to them, using data that was never originally organized into such formats and structures. The resulting scores can then be used in combination with brain imaging data (e.g., connectome data) to train one or more machine learning model(s) to automatically tag brain imaging data and/or the associated subjects for follow-up for at least one condition. This technology can be used for better diagnostic assessments of patients. For example, by using objective computations instead of subjective analysis, patients can be provided with a minimum level of care regardless of the skill level of a clinician or sequence of clinicians. This may be of particular value to patients that move, change insurance providers, or are otherwise forced to change clinicians before any one clinician is able to form a complete picture of the patient. For researchers, this technology can produce, for the first time, analysis from large-scale mining of records (e.g., EMRs) that can aid in the discovery and development of new clinical patterns that would be impossible to identify without the use of this technology. For example, researchers may perform automatic and very fast analysis of subpopulations to study the effect of various interventions (e.g., to compare the effectiveness of competing drugs or behavioral therapies). This can increase the speed and flexibility of both hypothesis generation and hypothesis testing. For both patients and caregivers, this technology may be used to continually or periodically monitor patients that may be known to be, or not yet known to be, at risk of negative impacts. That is to say, alerts may be set up to alert patients and/or caregivers if a patient is trending toward a negative impact such as risk of suicide, violence, substance abuse, etc. By continual monitoring of records, alerts may be raised early enough with a caregiver to prompt the caregiver to supplement their own subjective assessments with this technology's objective assessments to produce better outcomes than would be possible with subjective assessments alone.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

A computer system accesses historical electronic records such as medical records of a patient receiving behavioral therapy from a clinician. The computer system applies natural language processing procedures to identify terms in the records that are related to various dimensions of behavioral classifications, and scores these words based on intensity. This produces values in a first scale, and the computer system rescales them to different scales that are used in pre-existing dimensions of the behavioral classification. For example, the computer system can use these processes to categorize a subject into a behavioral category from Diagnostic and Statistical Manual of Mental Disorders, Fifth Edition, among other sources of classifications.

Figure 1:
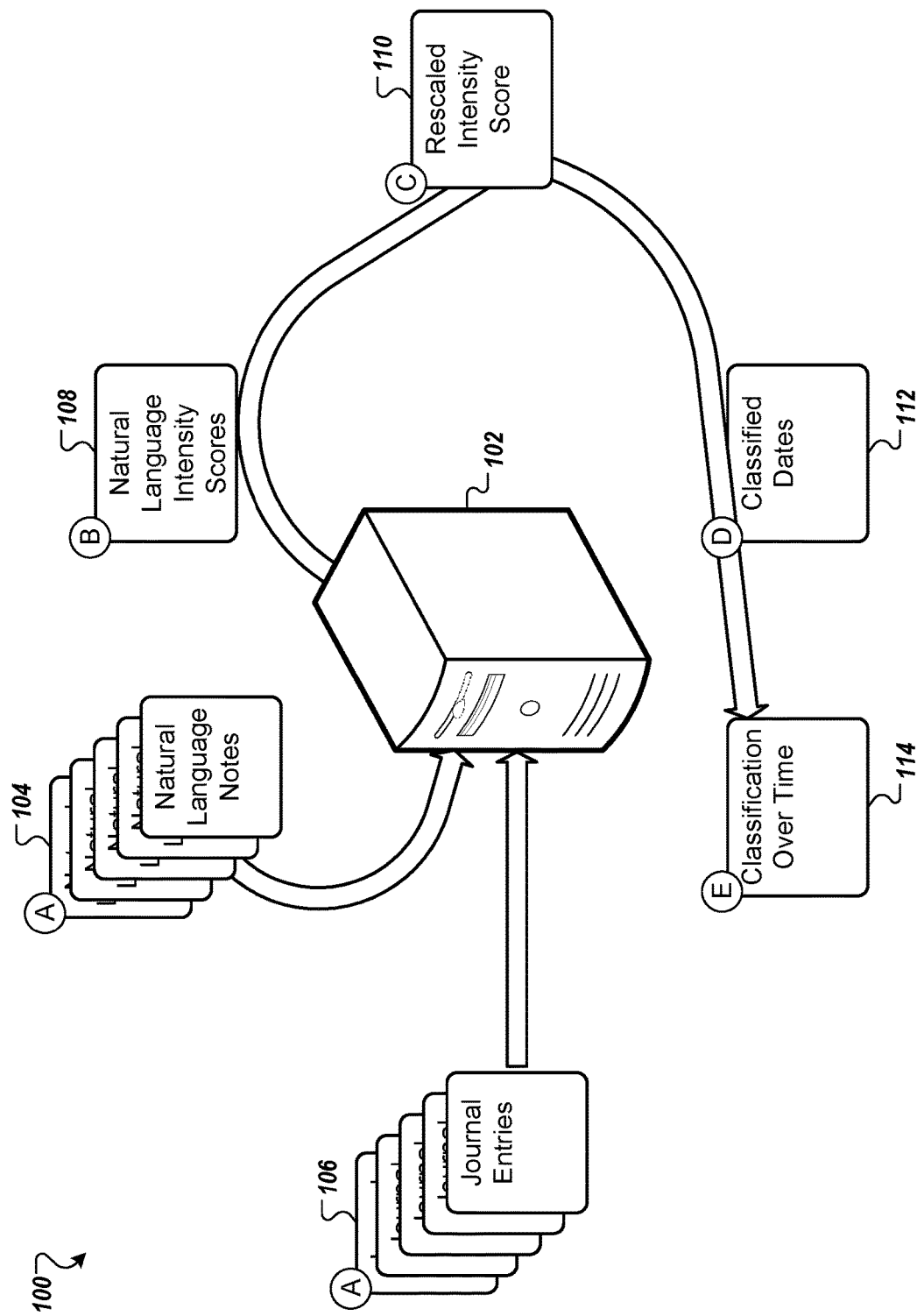
FIG. 1 shows an example system usable to classify a subject.

FIG. 1 shows an example system 100 usable to classify a subject. In the system 100, a computer system 102 accesses electronic records, applies natural-language processing to the records, and classifies a subject discussed in the natural language of the records.

The computer system 102 includes one or more real or virtual computing devices with memory and processors that execute instructions to perform computations. The system can also include networking components to connect various elements of the system, etc. In some cases, the computer system 102 can include a distributed set of servers and one or more clients that send data to the servers and request execution on the data.

The computer system 102 receives data about a subject. In general, the data about the subject can include natural-language text written by one or more people about the subject. For example, a clinician treating the subject can keep notes from therapy sessions stored as natural-language notes 104. In another example, the subject may keep a journal of their behaviors and experiences, stored in journal entries 106. The data 104 and 106 may be generated informally or 'spur-of-the-moment' in natural language without an attempt to specifically record clinically-accepted key words associated with a particular behavioral classification. However, technology described in this document can convert those natural-language elements into data that can be used to classify a subject into a pre-existing, formal category behavior. For example, medical texts such as the Diagnostic and Statistical Manual of Mental Disorders, Fifth Edition, contains many behavioral categories tied to specific jargon words and scales of intensity of different size (i.e. some scales are 1-2, some are 1-5, some are 1-10, etc). These jargon words may have a large number of natural-language synonyms. The computer system 102 can examine the data 104 and 106 for those synonyms, score them for intensity, and convert them into values of the scales used by the categories.

The computer system 102 can generate natural-language intensity values 108. In general, the natural-language intensity values 108 record a measure of how intense a particular token (e.g., word, phrase) is in natural use (e.g., as opposed to how intense the same token is understood to be in specialized jargon). In one example, "happy" may have a lower intensity score than "ecstatic", and similarly "busy" may have a lower intensity value than "frantic". In many cases, a single intensity scale may be used for every token, even tokens of different domains. That is to say, an intensity scale of 0 to 1 may be used, with "happy" and "busy" having values of 0.2 while "ecstatic" and "frantic" may having values of 0.8. For example, a lexical and rule-based sentiment analysis tool may be trained to sum valence scores of each work in a lexicon, adjusted according to a rule-set, and then normalized between −1 and 1 or 0 and 1. As will be understood, these lexicons, rulesets, and normalization ranges may be configured to match specific implementation details chosen in other parts of the system to ensure compatibility.

The computer system 102 can generate rescaled-intensity scores 110. As various dimensions of various categories may use different scales, the computer system 102 can adjust the intensity scores 108 from their original scale to the scale of the dimension they apply to. For example, "happy" may be placed on a scale from 1-5 and receive a rescaled-intensity score 110 of 1.0 (i.e. the original 0.2 multiplied by the scale length of 5 here), while "busy may be placed on a scale from 1-10 and receive a rescaled-intensity score of 2.0 (i.e. the original 0.2 multiplied by the scale length of 10 here).

With the rescaled-intensity scores 110, the computer system 102 can categorize the subject into one or more of the classifications. For example, for a particular classification (e.g., Major Depressive Disorder), there may be 9 dimensions, and an aggregate score of 5 or more across all dimensions may classify the subject into the classification of depressed. In some cases, a classification strength may be determined. For example, a score of 3—may be considered marginal or subclinical, a score of 5-7 may be considered mid-grade, and a score of 7 and above (e.g., 9) can be considered high-grade.

The computer system may place the classification into dates or date ranges 112. For example, if the data 104 and 106 are time-stamped, the tokens from a single document (and thus at a single time) or from documents within a time range may be collected and used to categorize the subject. Then, the subject may be placed in that classification for that date or date range. In this way, the classified dates 112 may be collected to create classification over time 114 for a subject.

Figure 2:
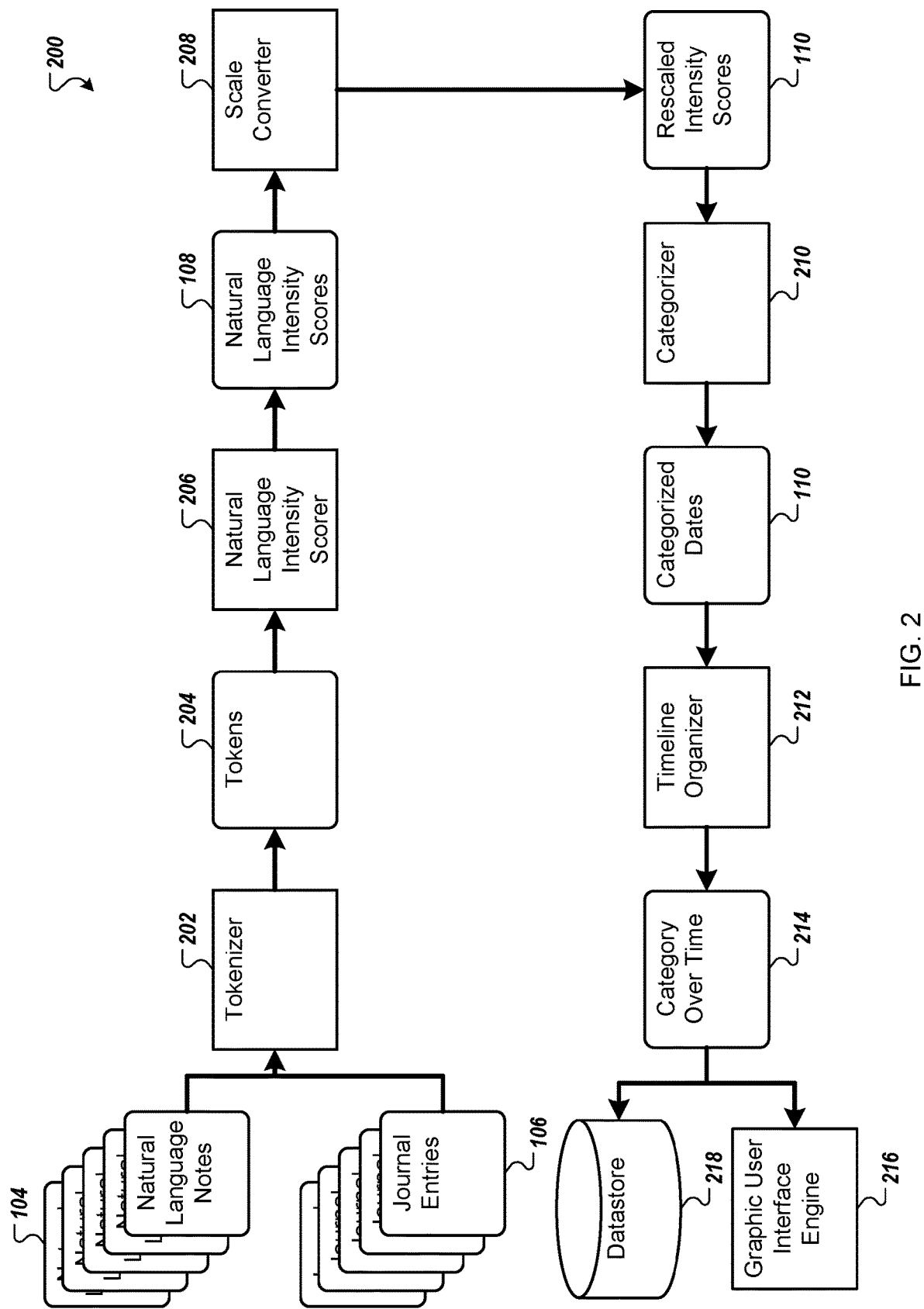
FIG. 2 shows an example data pipeline that receives data and produces data stored to disk and/or displayed in a graphical user interface (GUI).

FIG. 2 shows an example data pipeline 200 that receives data and produces data stored to disk and/or displayed in a graphical user interface (GUI). The data pipeline 200 may be used, for example, by the computer system 100 in order to categorize a subject into one or more behavioral categories based on natural-language data. The pipeline 202 describes a number of modules, shown in rectangular boxes with sharp corners, which receive and generate data, shown in rectangular boxes with rounded corners.

The pipeline 200 receives the data 104 and 106. This data 104 and 106 can be collected from one source, or may be collected from multiple sources. One example source of the data 104 and 106 is electronic medical records (EMRs) stored in a patient-management system that manages EMRs for many patients. For example, the subject may be a particular patient receiving therapy from a clinic that treats hundreds of patients. Each of the patients may have EMR that are specific to the patient, and the pipeline 200 may receive only those EMR associated with the subject, that the subject has consented for use in this way.

One example source of the data 104 and 106 is electronic records of notes written by a clinician for the subject. In some cases, these can be included as part of the EMR discussed previously. In some cases, these may be stored in formats other than EMRs. For example, a clinician may record notes during therapy with a pen and paper and then summarize the notes electronically afterward. The data 104 and 106 can be generated by scanning the pen-and-paper notes, applying object character recognition (OCR) to the scanned documents, and using the OCR text.

One example source of the data 104 and 106 is documents written by the subject. For example, a subject may keep a journal in which they document their emotions, actions, environment, etc. These journal entries may be used as the data 104 and 106. In addition or in the alternative, other writings of the subject such as email, social-media posts, or fiction may be collected and used as the data 104 and 106.

A tokenizer 202 can receive the data 104 and 106 to generate a set of tokens 204. In general, tokens 204 are collections of characters partitioned into units on which natural-language processes can be performed. In some examples, tokens may be single words, strings of works, and/or portions of words. The tokenizer 202 can receive a complete text expected to contain many tokens (e.g., a narrative entry in an EMR, a journal entry for a given day) and iterate through the characters of the text to identify a break between tokens. For example, space characters and certain punctuation may be identified by the tokenizer 202 to identify the beginning or end of a token.

In some cases, the some or all of the data 104 and 106 may include timestamps or other temporal information. The tokenizer 202 can identify, for each token, a timestamp from the electronic data 104 and 106. In such cases, the tokens 204 can be tagged with the timestamp of the source data 104 and 106 in which it occurs.

A natural language intensity scorer 206 can receive the tokens 204 and, for each token, generate a natural language intensity score 108. For example, the natural language intensity scorer 206 may store a table of token or sub-token strings along with a corresponding intensity value along a first scale (e.g. 0 to 1, 1 to 100). When a token 204 is received, the natural language intensity scorer 206 can match the token to a token or sub-token on the table and return the corresponding value.

A scale converter 208 can convert the natural language intensity scores 108 to the rescaled intensity scores 110. For example, the scale converter 208 can receive, as input, a natural language intensity score 108, the original scale range for the natural language intensity score 108, and target range to rescale too. This target range may be, for example, the scale of one of the dimensions of a classification from a group of pre-defined behavioral classification. In some cases, this process may be repeated so that each and every natural language intensity score 108 has corresponding 110 rescaled intensity scores 110 for each dimension. In some cases, each token 204 may be examined to match it with only a subset of related dimensions, and rescaled intensity scores 110 may be generated only for the matching dimensions. For example, a dimension of clinical depression may be "anxiety". In such a case, the tokens "anxious" and "panic" may be matched to the anxiety dimension, while the tokens "shoe" and "sky" may not be matched. Examples of tokens used for matching can be found later in this document.

A categorizer 210 can use the rescaled intensity scores 110 and their corresponding timestamps from the data 104 and 106 to create the categorized dates 110. For some subjects, the categorizer may record that, for all dates, the subject is not classified into any of the pre-existing behavioral classifications. Often, a subject will be classified into only one or a small percentage of the possible classifications. However, there may be subjects for whom the data 104 and 106 indicates classification into many categories. In some examples, the categorizer 210 can generate categorized dates 110 that include a strength value (e.g., mild vs heavy).

The categorizer 210 may include stored data that defines dimensions that are each part of a category from a list of possible categories used by a clinician of the subject, each category having a plurality of dimensions. One example category, depression, is listed at the end of this document along with its dimensions. For each dimension, a token or sub-token is listed. When a token 202 matches a token or sub-token in the list, the intensity of the token is included in the running score for that dimension for that category for the subject. For example, the token "anxious" would increase the value for the "anxiety" dimension, while "calm" would decrease the "anxiety" dimension. One such scheme for this inclusion of value is an average of intensity of all tokens. Another scheme may include weighing some tokens, for example, by a recency value, by their location in a text, etc.

A timeline organizer 212 can use the categorized dates 110 to generate categories over time 214 for the subject. For example, the timeline organizer may arrange the categories, and corresponding strengths, in a timeline to show change in categorizations and strength over time for the subject based on the data 104 and 106.

A GUI engine 216 can generate one or more GUIs showing the categories over time 214. For example, the GUI engine 216 may generate webpages or native application interfaces shown numerical information, graphs, or other data. One such example GUI is shown in FIG. 5. The GUI engine can send an alarm when a category reaches a threshold level set on a category by category basis.

A datastore 218 can store the categories over time 214, and any other data in the pipeline 200, for use by other computing systems. For example, the datastore 218 may be part of an EMR for the subject in a patient-management system.

Figure 3:
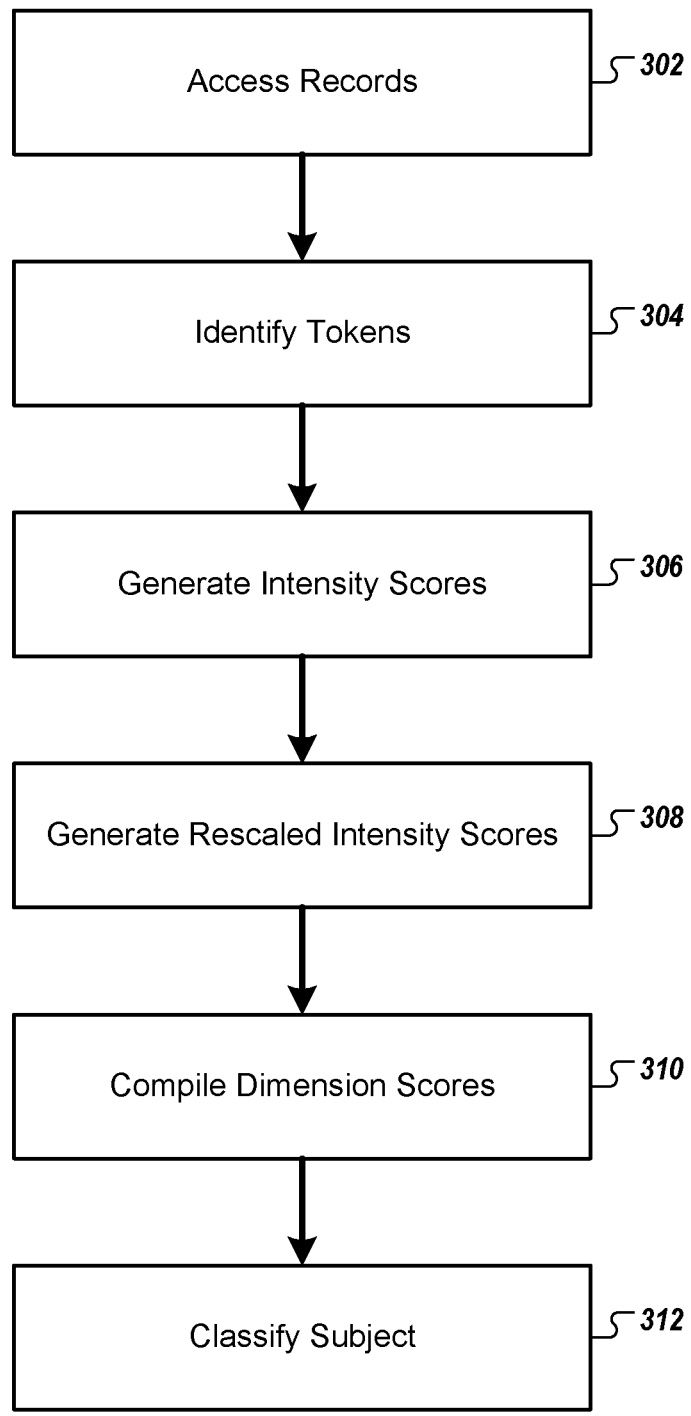
FIG. 3 shows an example process for generating classifications.

FIG. 3 shows an example process 300 for generating classifications. The process 300 can be performed, for example, by the computer system 100 using the pipeline 200 and will therefore be described with reference to the computer system 100 using the pipeline 200. However, other systems may be used to perform the process 300 or similar processes.

Records are accessed 302. For example, the computer system 102 and access, from computer storage, electronic records for a given subject, wherein the electronic records include natural language notes about the subject. These can include the data 104 and 106 as well as data from other sources.

Tokens are identified 304. For example, the computer system 102 can identify tokens in the natural language notes. In some cases, the tokenizer 202 can parse text document looking for stop characters that indicate the end and beginning of a token. Example stop characters include, but are not limited to, periods, spaces, and commas.

The tokenizer 202 can initially generate a list of all possible-tokens in the data 104 and 106. Then, the tokenizer 202 can select some, but not all of the possible-tokens. For example, the tokenizer 202 (or another element of the pipeline 200) can identify tokens that are a match with a particular dimension or all dimensions of one or all possible categories.

Intensity scores are generated 306. For example, the computer system 102 can generate, for each token or each token matching a dimension, a corresponding intensity score representing an intensity of match between the token and a particular dimension. As will be understood, these intensity scores may be domain-neutral and represent a general intensity and do not necessarily indicate a closeness or nearness-of-fit with a particular category or dimension of category.

Resealed-intensity scores are generated 308. For example, the computer system 102 can generate rescaled-intensity scores from the intensity scores by rescaling the intensity scores from the first scale to a second scale different from the first scale. That is to say, for each scored token, the score can be adjusted based on the scale used by the categories that are of interest and used by the computer system 102.

In some cases, this can include only generating rescaled-intensity scores for intensity scores that are greater than a threshold value. For example, tokens with intensity values below a particular threshold (e.g., 0.1 on a scale of 0 to 1) may be discarded. This may exclude, for example, data in which a large number of low intensity tokens are found.

Dimension scores are compiled 310. For example, the computer system 102 can compile for each dimension of each category, a dimension-score based on the intensity scores. In some cases, this may include adding together the intensity scores of tokens matching the dimensions. In some cases, this may include finding an average of the intensity scores of tokens matching the dimension.

The subject is categorized 312. For example, the computer system 102 can categorize the subject into at least one category based on the dimension scores. This may include, for example, identify categories for which the various dimensions all have dimension-scores above corresponding threshold values.

Figure 4:
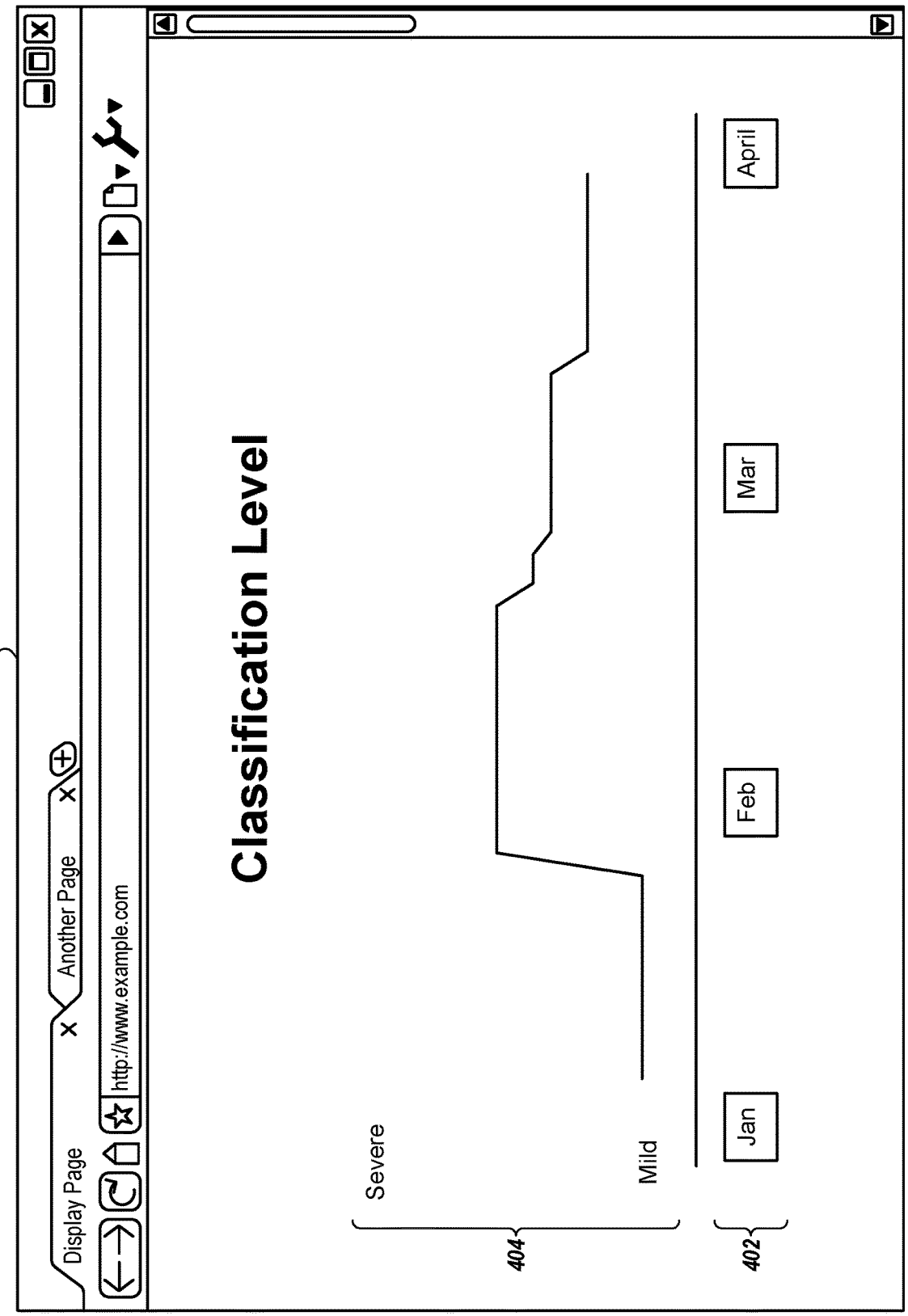
FIG. 4 shows an example GUI.

FIG. 4 shows an example GUI 400. The GUI 400 is shown here as a webpage rendered in a web browser, but other formats of GUIs are possible. The GUI 400 includes a timeline 402 along which a trend line 404 of classification strength is shown for a given classification (e.g., depression, addiction, autism spectrum disorder, bipolar disorder, etc).

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

One example category, depression, is listed at the end of this document along with its dimensions. For each dimension, token(s) and/or sub-token(s) is/are listed:

anxiety:
  positive:
    anxious
    anxiety
    worri
    panic
    fear
    uneasiness
  negative:
    calm
    still
delusions:
  positive:
    delusion
    false beli
    fantasy
    paranoia
    preoccupation
    suspicious
    persecut
    hostile
    somatic concern
    unusual tought
disorg_speech:
  negative:
    coherent
  positive:
    disorganized speech
    derailment
    incoherence
disorganized:
  negative:
    organized
  positive:
    disorganized
    catatonic
    stupor
    excit
    restless disorientation
bizarre behavio
conceptual disorg
anxiety
  grandios
mannerism
poor attention
thought disorder
movement disorder
fatigue:
negative:
  energy
positive:
  fatigue
  anergia
  tired
food:
negative:
  weight
  appetite
  food
positive:
  weight
  loss of appetite
  food
  cravings
hallucinations:
positive:
  hallucination
  hallucinate
  hallucinatory
interest:
negative:
  interest
  pleasure
  sex
  hobbies
  sport
positive:
  anhedonia
irritability:
positive:
  irrita
mood:
negative:
  happy
  mood
  interest
positive:
  depress
  sad
  irrita
  anxi
  cry
  glum
  downcast
  unhappy
  sadness
  sad
  tearful
  empty
  empti
  hopeless
  frustration
muscle:
positive:
  muscle pain muscle tension
  stiff muscle
  muscles tension
  muscles pain
negsym:
negative:
  move
  speak
  motivated
  spontaneity
  conversation
  coperative
  attention
positive:
  affective flattening
  alogia
  avolition
  mute
  unmotivated
  uncooperative
  apath
  withdraw
  blunt
  poor rapport
  stereotyped thinking
  motor retardation
  depression
  poor attention
  avoidance
  immobility
  flat affect
  reduced feeling
psych:
positive:
  psychomotor retardation
  slow
restless:
negative:
  rest
  relax
positive:
  restless
  on the edge
sleep:
negative:
  sleep
  slept
  staying asleep
  falling asleep
positive:
  insomnia
  hypersomnia
  difficulty falling asleep
  difficulty speeling
  unstatisfying sleep
  restless
  sleep disturbance
suicide:
negative:
  live
  living
positive:
  death
  suicide
  self-harm
  death
concentration:

negative:
  concentrate
  think
  focus
positive:
  indecisiv
  inattentive
  mind going blank
worthless:
negative:
  esteem
positive:
  worthless
  hopeless
  guilt

What is claimed is:

1. A method comprising:
accessing, from computer storage, electronic records for a given subject, wherein the electronic records include natural language notes about the subject;
identifying tokens in the natural language notes;
generating, for each token, a corresponding intensity score representing an intensity of match between the token and a particular dimension, wherein the intensity scores are each values on a first scale range, wherein each dimension is one of a plurality of dimensions of a category out of a plurality of categories;
determining whether the intensity score corresponding with each token is greater than a threshold value;
for the intensity score is greater than the threshold, generating rescaled-intensity scores from the intensity scores by rescaling the intensity scores from the first scale range to a second scale range different from the first scale range and discarding the tokens with intensity scores equal to or below the threshold;
compiling, for each dimension of each category, a dimension-score based on the rescaled-intensity scores; and
categorizing the subject into at least one category based on the dimension scores.

2. The method of claim 1, wherein the electronic records are electronic medical records (EMRs) stored in a patient-management system that manages EMRs for many patients.

3. The method of claim 1, wherein the electronic records comprise documents written by the subject.

4. The method of claim 1, wherein the natural language notes comprise natural language notes written by a clinician of the subject.

5. The method of claim 1, wherein identifying tokens in the natural language notes comprises:
generating a list of all possible-tokens in the natural language notes; and
selecting some, but not all of the possible-tokens based on a match with a particular dimension.

6. The method of claim 5, wherein the particular dimension is one dimension that is part of a category from a list of possible categories used by a clinician of the subject, each category having a plurality of dimensions.

7. The method of claim 6, wherein the second scale is associated with anxiety, the second scale range spans from 0 to 9 and the particular category is "Major Depressive Disorder".

8. The method of claim 1, wherein the tokens comprise words, strings, and portions of words.

9. The method of claim 1, wherein the first scale range spans from 0 to 1.

10. The method of claim 1, wherein:
the electronic records include timestamps;
identifying, for each token, a timestamp from the electronic records; and
the method further comprises generating a time-series of the rescaled-intensity scores that reflect changes in the subject over time.

11. A system comprising:
one or more computers and one or more storage devices on which are stored instructions that are operable, when executed by the one or more computers, to cause the one or more computers to perform operations comprising:
accessing, from computer storage, electronic records for a given subject, wherein the electronic records include natural language notes about the subject;
identifying tokens in the natural language notes;
generating, for each token, a corresponding intensity score representing an intensity of match between the token and a particular dimension, wherein the intensity scores are each values on a first scale range, wherein each dimension is one of a plurality of dimensions of a category out of a plurality of categories;
determining whether the intensity score corresponding with each token is greater than a threshold value;
for the intensity score is greater than the threshold, generating rescaled-intensity scores from the intensity scores by rescaling the intensity scores from the first scale range to a second scale range different from the first scale range and discarding the tokens with intensity scores equal to or below the threshold;
compiling, for each dimension of each category, a dimension-score based on the rescaled-intensity scores; and
categorizing the subject into at least one category based on the dimension scores.

12. The system of claim 11, wherein the electronic records are electronic medical records (EMRs) stored in a patient-management system that manages EMRs for many patients.

13. The system of claim 11, wherein the electronic records comprise documents written by the subject.

14. The system of claim 11, wherein the natural language notes comprise natural language notes written by a clinician of the subject.

15. The system of claim 11, wherein identifying tokens in the natural language notes comprises:
generating a list of all possible-tokens in the natural language notes; and
selecting some, but not all of the possible-tokens based on a match with a particular dimension.

16. The system of claim 15, wherein the particular dimension is one dimension that is part of a category from a list of possible categories used by a clinician of the subject, each category having a plurality of dimensions.

17. The system of claim 16, wherein the second scale is associated with anxiety, the second scale range spans from 0 to 9 and the particular category is "Major Depressive Disorder".

18. The system of claim 11, wherein the tokens comprise words, strings, and portions of words.

19. The system of claim 11, wherein the first scale range spans from 0 to 1.

20. The system of claim 11, wherein:
the electronic records include timestamps;
identifying, for each token, a timestamp from the electronic records; and
the operations further comprises generating a time-series of the rescaled-intensity scores that reflect changes in the subject over time.

21. One or more non-transitory computer-readable storage media encoded with instructions that, when executed by one or more computers, cause the one or more computers to perform operations comprising:
- accessing, from computer storage, electronic records for a given subject, wherein the electronic records include natural language notes about the subject;
- identifying tokens in the natural language notes;
- generating, for each token, a corresponding intensity score representing an intensity of match between the token and a particular dimension, wherein the intensity scores are each values on a first scale range, wherein each dimension is one of a plurality of dimensions of a category out of a plurality of categories;
- determining whether the intensity score corresponding with each token is greater than a threshold value;
- for the intensity score is greater than the threshold, generating rescaled-intensity scores from the intensity scores by rescaling the intensity scores from the first scale range to a second scale range different from the first scale range and discarding the tokens with intensity scores equal to or below the threshold;
- compiling, for each dimension of each category, a dimension-score based on the rescaled-intensity scores; and
- categorizing the subject into at least one category based on the dimension scores.

* * * * *